(12) United States Patent
Saralaya et al.

(10) Patent No.: US 9,169,232 B2
(45) Date of Patent: Oct. 27, 2015

(54) 3-(5-METHYL-2-OXO-L, 3-DIOXOL-4-YL) METHYLOXY-2-TRANS-[(4-CHLORO PHENYL) CYCLOHEXYL][1,4]NAPHTHAQUINONE-ATOVAQUONE PRODRUG

(75) Inventors: Sanjay Sukumar Saralaya, Bangalore (IN); Akshaya Kunjyannaya, Bangalore (IN); Shashiprabha, Bangalore (IN); Shridhara Kanakamajalu, Bangalore (IN); Kothapalli Sundarraja Rao, Bangalore (IN); Kuppuswamy Nagarajan, Bangalore (IN)

(73) Assignee: Alkem Laboratories Limited, Mumbai (IN)

( * ) Notice: Subject to any disclaimer, the term of this patent is extended or adjusted under 35 U.S.C. 154(b) by 0 days.

(21) Appl. No.: 14/344,644

(22) PCT Filed: Sep. 14, 2012

(86) PCT No.: PCT/IN2012/000613
§ 371 (c)(1),
(2), (4) Date: Mar. 13, 2014

(87) PCT Pub. No.: WO2013/093937
PCT Pub. Date: Jun. 27, 2013

(65) Prior Publication Data
US 2014/0343297 A1    Nov. 20, 2014

(30) Foreign Application Priority Data

Sep. 16, 2011 (IN) .......................... 747/MUM/2011

(51) Int. Cl.
*C07D 317/36* (2006.01)
*C07D 317/40* (2006.01)

(52) U.S. Cl.
CPC ............ *C07D 317/36* (2013.01); *C07D 317/40* (2013.01)

(58) Field of Classification Search
CPC .................................................... C07D 317/40
See application file for complete search history.

(56) References Cited

FOREIGN PATENT DOCUMENTS

WO    WO 91/04021    *    4/1991  ............. A61K 31/12

* cited by examiner

*Primary Examiner* — Erich A Leeser
(74) *Attorney, Agent, or Firm* — George W. Moxon, II; Brian Harrod

(57) ABSTRACT

The present invention relates to atovaquone prodrug compound of formula (I). Accordingly, present invention provides a process involving condensation of Atovaquone (II) with 5-methyl-4-chloromethyl dioxalone (III) in suitable solvent system and optionally followed by distillation and crystallization to provide Atovaquone prodrug compound of formula (I) in high yields, purity, and suitable for large-scale manufacture.

2 Claims, No Drawings

3-(5-METHYL-2-OXO-L, 3-DIOXOL-4-YL) METHYLOXY-2-TRANS-[(4-CHLORO PHENYL) CYCLOHEXYL][1,4]NAPHTHAQUINONE-ATOVAQUONE PRODRUG

FIELD OF THE INVENTION

The present invention relates to a prodrug of atovaquone.

BACKGROUND OF THE INVENTION

A wide range of naphthoquinones are known in the art. Such compounds have been variously described as having antimalarial, anticoccidial and antitheilerial activity. Some compounds have also been described as possessing activity against external parasites. Thus, Fieser et al, *J. Amer. Chem. Soc.* 1948, 70, 3156-3165 (and references cited therein) describe a large number of 2-substituted-3-hydroxy-1,4-naphthoquinones as having antimalarial activity. A number of these compounds have also been described in U.S. Pat. Nos. 2,553,647 and 2,553,648. Further classes of 2-substituted-3-hydroxy-1,4-naphthoquinones having activity as antimalarial, anticoccidial and/or antitheilerial agents are described in U.S. Pat. Nos. 3,367,830, and 3,347,742, U.K. Patent Specification No. 1553424, and European Patent Specifications Nos. 2228, 77551, 77550 and 123,238.

European Patent No. 123,238 discloses 2-substituted-3-hydroxy-1,4-naphthoquinones which are said to be active against the human malaria parasite *Plasmodium falciparum* and also against *Eimeria* species such as *E. tenella* and *E. acervulina*, which are causative organisms of coccidiosis. 2-Substituted-3-hydroxy-1,4-naphthoquinones (1) have been described in literature as possessing anti-protozoal activity, in particular anti-malarial. Anti-coccicidal activity has also been reported to a lesser extent. Hundreds of such compounds as possessing anti-malarial activity have been disclosed by Fieser and co-workers.

Many orally administered drugs display poor bio-availability when administered in conventional dosage forms. With several drugs, absorption may be as little as 30 per cent or less of the orally administered dose. To compensate for this effect, a very large dose is often administered so that absorption of the therapeutically required quantity of the drug can occur. This technique is costly with expensive drugs, and the non-absorbed drug may also have undesirable side effects within the gastrointestinal tract. In addition, the poorly absorbed drugs often display a great deal of variability between patients in bioavailability, and this can create dosing problems. This poor bioavailability is often associated with poor solubility of drugs. There are various techniques available to overcome solubility and bioavailability problem, and one such viable technique is particle size reduction. However particle size reduction adds another step to the process as well as added cost. Another approach to improving poor bioavailability by raising aqueous solubility of the drug is administering a pro-drug. Any compound metabolized in vivo to provide the bio-active agent is a prodrug. Prodrugs are therapeutic agents, inactive per se, but transformed into one or more active metabolites. Prodrugs are bioreversible derivatives of drug molecules used to overcome some barriers to the utility of the parent drug molecule. These barriers include, but are not limited to, solubility, permeability, stability, presystemic metabolism and targeting limitations Atovaquone has low oral bioavailability, which has been partly attributed to poor water solubility. It has also shown that an oral dosing of atovaquone has been complicated by variable plasma atovaquone levels, which were an important determinant of therapeutic outcome. In clinical trial with a conventional tablet formulation, it was observed that a therapeutic response against *Pneumocystis carinii* Pneumonia depended on steady-state levels in plasma. In order to overcome the problems associated with poor solubility and variable plasma atovaquone levels, prior art has used atovaquone of small particle size or has made atovaquone derivatives which may act like prodrugs of the same.

U.S. Pat. No. 6,649,659 relates to a process for the production of microfluidized particles of atovaquone having improved bioavailability. The patent discloses that microfluidised particles of atovaquone produced using a Microfluidiser, surprisingly, had improved bioavailability of the compound. The patent also provides small particles of atovaquone, wherein suitably at least 90% of the particles have a volume diameter in the range of 0.1-3 µm. Preferably at least 95% of the particles have a volume diameter in the range 0.1-2 µm.

Hage et al., *European Journal of Medicinal Chemistry*, 44(11), 4778-4782 (2009) discloses the synthesis and antimalarial activity of new atovaquone derivatives were designed which was substituted at the 3-hydroxy group by ester and ether functions. The compounds were evaluated in vitro for their activity against the growth of *Plasmodium falciparum*, the malaria causing parasite. All the compounds showed potent activity, with IC50 values in the range of 1.25-50 nM, comparable to those of atovaquone and much higher than chloroquine or quinine.

Comley et al., *Antimicrobial agent and Chemotherapy*, 39, 2217-2219 (1995) states the prophylactic efficacy of 17C91, a carbamate prodrug of Atovaquone was investigated in a severe combined immunodeficient mouse model of *Pneumocystis carinii* pneumonia (PCP). At an oral dosage equivalent to 100 mg of Atovaquone per Kg of body weight per day, 17C91 protected 9 of 10 mice from PCP and had a Prophylactic efficacy comparable to that of co-trimoxazole (at 250 mg of sulfamethoxazole plus 50 mg of trimethoprim per kg per day orally). The intensity of *P. carinii* infection (infection score) of mice treated with 17C91 correlated with the concentration of Atovaquone in the plasma, with clearance of the infection associated with plasma Atovaquone levels of >35 µ/ml. 17C91 given orally provided enhance levels of Atovaquone in the plasma compared with the conventional Atovaquone formulation. Additional studies reported in this paper demonstrate that the Prophylactic activity 17C91 against PCP in severe combined immunodeficient mice is comparable to that of a new oral microparticulate formulation of Atovaquone.

Karaman et al., *Chem Biol Drug Des*, 76, 350-360 (2010) discloses computer-assisted design of Pro-drugs for antimalarial atovaquone, the density functional theory (DFT) and ab initio calculation results for the proton transfer reaction in Kirby's enzyme models 1-6 reveal that the reaction rate is largely dependent on the existence of a hydrogen bonding net in the reactants and the corresponding transition states. Further, the distance between the two reacting centers and the angle of the hydrogen bonding formed along the reaction path has profound effects on the rate. Hence, the study on the system reported herein could provide a good basis for designing antimalarial (Atovaquone) prodrug system that can be used to release the parent drug in a controlled manner. For example, based on the calculated log EM, the cleavage process for prodrug 1Pro may be predicted to be about $10^{11}$ times faster than that for a prodrug 4Pro and about $10^4$ times faster than prodrug 2Pro: $rate_{1Pro} > rate_{2Pro} > rate_{4Pro}$. Thus, the rate by which the prodrug releases the antimalarial drug can be determined according to the nature of the linker.

The present inventors have now found a new compound as a prodrug of Atovaquone, in order to overcome the problems associated with solubility and variable bioavailability of atovaquone. The Atovaquone prodrug of the present invention is expected to provide better solubility than atovaquone and non-variable plasma levels of atovaquone as compared to the levels obtained after administration of atovaquone.

We have synthesized a compound of formula (I) i.e., 3-(5-methyl-2-oxo-1,3-dioxol-4-yl)methyloxy-2-trans-[(4-chlorophenyl)cyclohexyl][1,4] naphthaquinone by using atovaquone (II) and 5-methyl-4-chloromethyl dioxalone (III) using the route shown in Scheme 1.

OBJECT OF THE INVENTION

It is an object of the present invention to provide the compound of formula (I).

It is further object of the present invention to provide a process involving condensation of Atovaquone (II) with 5-methyl-4-chloromethyl dioxalone (III) in a suitable solvent system and optionally followed by distillation and re-crystallization to give Atovaquone prodrug compound of formula (I).

Another object of the present invention to provide a process for preparation of Atovaquone prodrug compound of formula (I) in high yields and purity, suitable for large-scale manufacturing.

SUMMARY OF THE INVENTION

According to one aspect of the present invention, the compound of formula (I) is provided.

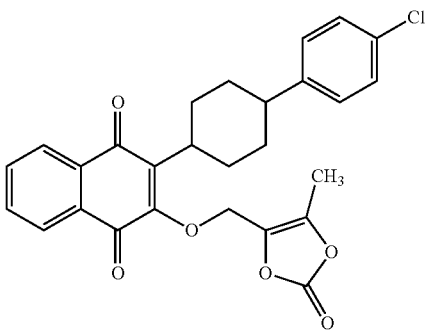 [SMILES: Cc1oc(=O)oc1COC1=C(C2CCC(c3ccc(Cl)cc3)CC2)C(=O)c2ccccc2C1=O]

Compound of Formula (I)

Accordingly, present invention provides a process involving condensation of Atovaquone (II) with 5-methyl-4-chloromethyl dioxalone (III) in suitable solvent system and optionally followed by distillation and crystallization to provide Atovaquone prodrug compound of formula (I).

According to another aspect of the present invention, a process for preparation of Dioxalone Atovaquone prodrug compound of formula (I) in high yields and purity, suitable for large-scale manufacturing is provided.

The invention may be summarized as follows:
A. A compound of formula (I),

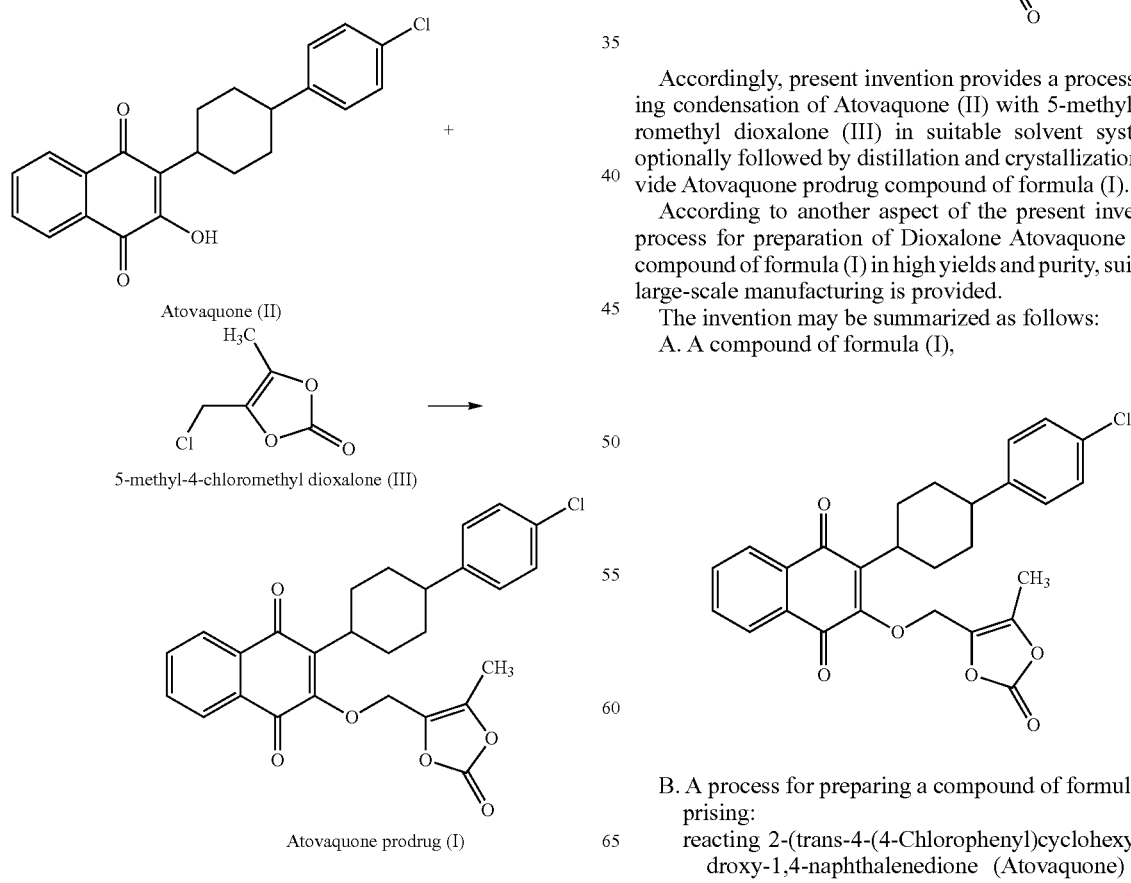

Scheme 1

B. A process for preparing a compound of formula I comprising:
reacting 2-(trans-4-(4-Chlorophenyl)cyclohexyl)-3-hydroxy-1,4-naphthalenedione (Atovaquone) of formula (II)

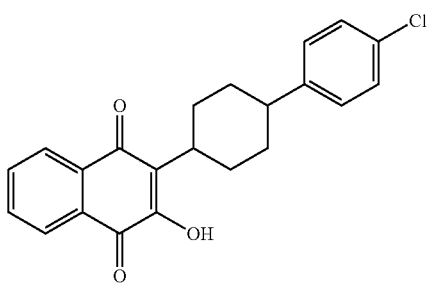 [SMILES: O=C1C(O)=C(C2CCC(c3ccc(Cl)cc3)CC2)C(=O)c2ccccc21]

with 5-methyl-4-chloromethyldioxalone of formula (III)

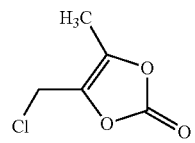

in the presence of a solvent, to form the compound of formula (I).

DETAILED DESCRIPTION OF THE INVENTION

Before the present process and methods are described, it is to be understood that this invention is not limited to particular compounds, formulas or steps described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a compound" includes a plurality of such compounds and reference to "the step" includes reference to one or more step and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In accordance with the present invention, there is provided a compound of formula (I) is provided.

Compound of Formula (I)

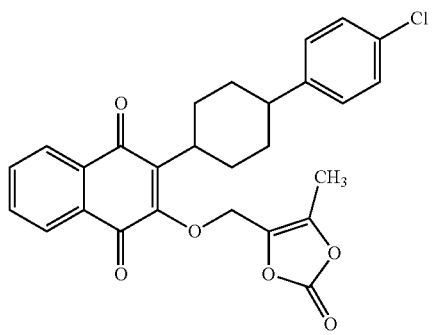

The compound of Formula I is a prodrug of atovaquone and is chemically 3-(5-methyl-2-oxo-1,3-dioxol-4-yl)methyloxy-2-trans-[(4-chlorophenyl)cyclohexyl][1,4]naphthaquinone.

In accordance with the present invention, there is provided a condensation of Atovaquone (II) with 5-methyl-4-chloromethyl dioxalone (III) in suitable solvent system and followed by distillation and crystallization to provide Atovaquone prodrug 3-(5-methyl-2-oxo-1,3-dioxol-4-yl)methyloxy-2-trans-[(4-chlorophenyl)cyclohexyl][1,4]naphthaquinone of formula (I).

Both starting materials (II) and (III) are known and are disclosed in the specifications of U.S. Pat. No. 5,053,432 and of Japanese Laid open No. 57/203067, respectively.

Atovaquone used as starting material may be used in the form of a residue or a crystalline form, obtained by processes described in the art, for example by the process described in the U.S. Pat. No. 4,981,874. Atovaquone can also be obtained by a process described in the patentee's pending PCT application number WO20090122432. The process briefly involves a process for the preparation of Atovaquone,

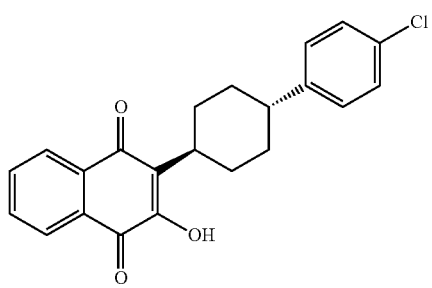 [SMILES: O=C1C(O)=C([C@H]2CC[C@H](c3ccc(Cl)cc3)CC2)C(=O)c2ccccc21]

comprising the steps of:
(i) condensing 2,3-dichloro-1,4-naphthoquinone of formula (A)

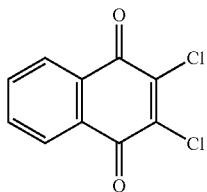

Formula (A)

with trans 4-(4-chlorophenyl)cyclohexane-1-carboxylic acid of formula (B)

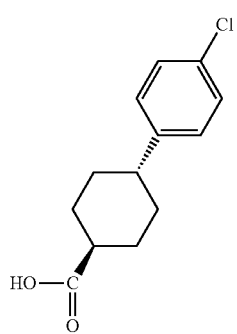

Formula (B)

in presence of silver nitrate and ammonium persulfate in a suitable solvent to provide 2-[4-(4-chlorophenyl)cyclohexyl]-3-chloro-1,4-naphthoquinone of formula (C),

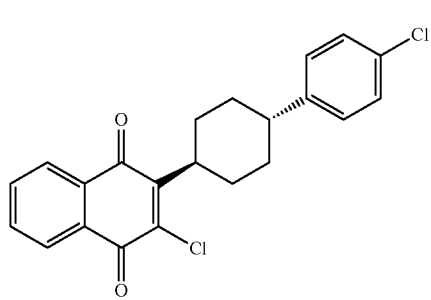

(C)

(ii) treating 2-[4-(4-chlorophenyl)cyclohexyl]-3-chloro-1,4-naphthoquinone of formula (C) with a base in a solvent and followed by treatment with an acid to provide Atovaquone.

The prepared compound (I) as such can be isolated and purified by a known method per se such as, for example, concentration, pH conversion, transfer to another solvent, extraction with a solvent, crystallization, recrystallization, fractional distillation, chromatography.

In accordance with the present invention, said reaction is carried out in the solvent selected from the group comprising substituted, unsubstituted, cyclic, bicyclic, saturated, or unsaturated, straight or branched hydrocarbon but not limited to aliphatic or aromatic hydrocarbon, having $C_6$-$C_{10}$ atoms, water, aliphatic nitrile, ketones, esters, ethers and chlorinated solvents, or mixtures thereof. The solvent used in the present invention is selected from the group consisting of hexane, toluene; esters such as ethyl acetate, propyl acetate, isopropyl acetate, butyl acetate and isobutyl acetate; water; aliphatic nitrile such as acetonitrile and propionitrile; ketones such as acetone, methyl ethyl ketone, methyl isobutyl ketone and diethyl ketone; ethers such as tetrahydrofuran and dioxane; and chlorinated solvents such as methylene chloride, chloroform, carbontetrachloride and ethylene dichloride; and the like or mixtures thereof. The said above solvents may also used for the preparing dioxalone prodrug of Atovaquone in one or more solvents of a first type and/or one or more anti-solvent of a second type.

In accordance with the present invention, there is provided a process for preparation of Atovaquone prodrug compound of formula (I) or solvates thereof in high yields and purity, suitable for large-scale manufacturing.

In a further aspect, the invention thus provides new compound which is a prodrug of Atovaquone for use in treating *Pneumocystis carinii*, Plasmodia, and tachyzoite and cyst forms of *Toxoplasma gondii*, either alone or in combination with other anti malarial agents. In the practice of the invention, the most suitable route of administration as well as the magnitude of a therapeutic dose of dioxalone prodrug of Atovaquone in any given case will depend on the nature and severity of the disease to be treated. The dose, dose frequency may also vary according to the age, body weight and response of the individual patient.

The invention thus also provides pharmaceutical compositions containing prodrug of Atovaquone which may optionally contain other crystalline forms and/or other active pharmaceutical drugs. In addition to the active ingredient(s), the pharmaceutical compositions of the present invention can contain one or more commonly used pharmaceutical excipients. Pharmaceutical compositions include those suitable for oral and parenteral (including subcutaneous, intradermal intramuscular and intravenous) administration as well as administration by naso-gastric tube. Suitable formulations within the scope of the present invention include, for example, solid dosage forms such as tablets and liquid dosage forms, such as suspensions, which are preferred formulations.

The Atovaquone prodrug compound of formula (I) of the present invention overcomes the problems associated with poor solubility and variable bioavailability of atovaquone. The Atovaquone prodrug of the present invention provides better solubility than atovaquone and non-variable plasma levels of atovaquone as compared to the levels obtained after administration of atovaquone. In-vitro and animal study using the prodrug of the invention showed the prodrug of atovaquone had toxicity in the acceptable range.

The following examples are intended to illustrate the scope of the present invention in all its aspects but not to limit it thereto.

Reference Example 1

Process for the Preparation of Atovaquone

2-[4-(4-Chlorophenyl)cyclohexyl-3-chloro-1,4-naphthoquinone (20 gm) was added to methanol (400 ml) at 25-30° C., the contents were heated to reflux and then potassium hydroxide solution (20 gm) in water (200 ml) was slowly added for 30 minutes at reflux. The reaction mass was stirred for 6 hours at reflux, to the resulting mass added hydrochloric acid (72 ml) slowly for 15 to 20 minutes at reflux and then cooled to 25-30° C. The resulting mass was further cooled to 0° C. and then stirred for 1 hour at 0-5° C. The solid was filtered, washed with water and then dried at 50-60° C. to give 18.1 gm of atovaquone.

Example 1

Process for the Preparation of 3-(5-methyl-2-oxo-1,3-dioxol-4-yl)methyloxy-2-trans-[(4-chlorophenyl)cyclohexyl][1,4]naphthaquinone Atovaquone (1 equivalent, obtained by the process described in example 1 of the U.S. Pat. No. 4,981,874), Acetonitrile (20V), $K_2CO_3$ (2.5 equivalent) were charged to the reactor. Then 5-methyl-4-chloromethyldioxalone (2.5 equivalents) was added drop wise to the mass at room temperature. The mass was further heated to 60-65° C. for 16-18 hrs. The reaction was monitored by TLC. After the completion of the reaction, the solvent was distilled out completely under vacuum. Water (5V) and Ethyl acetate (5V) were added to the mass and stirred at RT for ½ hr. The mass was filtered under suction and suction for 2 hrs.

Yield: 60-62%
Purity: 98-99%

Example 2

Charged Atovaquone (1 equivalent, obtained by the process described in example 1 of the U.S. Pat. No. 4,981,874), Acetonitrile (20V), $K_2CO_3$ (2.5 equivalent) to the reactor fitted with a guard tube. Added 5-methyl-4-chloromethyldioxalone (2.5 eq) drop wise to the mass at room temperature. The mass was further heated to 60-65° C. for 16-18 hrs. Reaction was monitored by TLC. After the completion of the reaction, distilled of the solvent completely under vacuum. To the mass added water (10V) and Ethyl acetate (5V) and stirred the mass at room temperature for ½ hr. Filtered the heterogeneous mass under suction. Bed washed with 1V of Ethyl acetate. Suction dried the mass for 2 hrs. Dried the mass in Vacuum tray dryer (VTD) at 65-70° C. for 4 hrs.

Yield: 90%
Purity: 98.7%

Example 3

Charged Atovaquone (1 equivalent), $K_2CO_3$ (2.5 equivalent) and Acetonitrile (20 V) to a reactor fitted with a guard tube. Added 5-methyl-4-chloromethyldioxalone (2.5 equivalent) and heated to 60-65° C. for 16-18 hrs. After completion of the reaction distilled out the solvent completely and add a mixture of acetonitrile and water to the mass. Filter the solid and wash with acetonitrile and dried at 65-70° C. for 4 hrs.

Yield: 72.12%
Purity: 99%.

Example 4

Added Atovaquone (1 equivalent), $K_2CO_3$ (1.5 equivalent) and acetonitrile (20 V) to a reactor fitted with a guard tube. Added 5-methyl-4-chloromethyldioxalone (1.5 equivalent) and heated it to 60-65° C. for 16-18 hrs. After completion of the reaction distilled out the solvent completely and added a mixture of acetonitrile and water to the mass. Filtered the solid and washed with acetonitrile and dried at 65-70° C. for 4 hrs.

Yield: 62.8%
Purity: 93%

Example 5

Added Atovaquone (1 equivalent), $K_2CO_3$ (1.5 equivalent) and Acetonitrile (20 V) to a reactor fitted with a guard tube. Added 5-methyl-4-chloromethyldioxalone (1.0 equivalent) and heated it to 60-65° C. for 16-18 hrs. After completion of the reaction distilled out the solvent completely and added a mixture of acetonitrile and water to the mass. Filtered the solid and washed with acetonitrile and dried at 65-70° C. for 4 hrs.

Yield: 45.11%
Purity: 91%

Although the invention has been described in terms of particular embodiments and applications, one of ordinary skill in the art, in light of this teaching, can generate additional embodiments and modifications without departing from the spirit of or exceeding the scope of the claimed invention. It should be emphasized that the above-described embodiments of the present invention, particularly any "preferred" embodiments, are merely possible examples of the invention of implementations, merely set forth for a clear understanding of the principles of the invention. Accordingly, it is to be understood that the drawings and descriptions herein are preferred by way of example to facilitate comprehension of the invention and should not be construed to limit the scope thereof.

The invention claimed is:

1. A compound of formula (I),

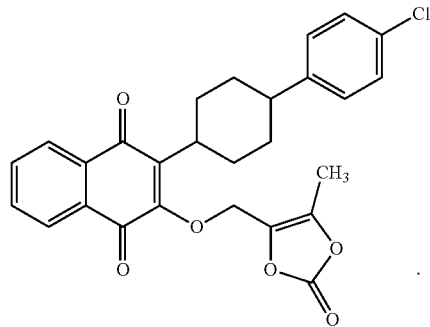 [SMILES: Cc1oc(=O)oc1COC1=C(C2CCC(c3ccc(Cl)cc3)CC2)C(=O)c2ccccc2C1=O]

2. A process for preparing a compound of formula I comprising:

reacting 2-(trans-4-(4-Chlorophenyl)cyclohexyl)-3-hydroxy-1,4-naphthalenedione (Atovaquone) of formula (II)

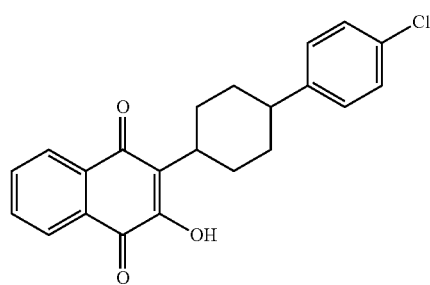 [SMILES: O=C1C(O)=C(C2CCC(c3ccc(Cl)cc3)CC2)C(=O)c2ccccc21]

with 5-methyl-4-chloromethyldioxalone of formula (III)
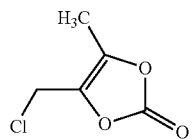
in the presence of a solvent, to form the compound of formula (I).
* * * * *